(12) United States Patent
Chau et al.

(10) Patent No.: US 9,138,171 B2
(45) Date of Patent: Sep. 22, 2015

(54) SYSTEM AND METHOD FOR DETECTING SWALLOWING ACTIVITY

(75) Inventors: Thomas T. K. Chau, Toronto (CA); David J. Kenny, Toronto (CA); Michael J. Casas, Toronto (CA); Glenn Berall, Toronto (CA)

(73) Assignee: Holland Bloorview Kids Rehabilitation Hospital, Toronto (CA)

(*) Notice: Subject to any disclaimer, the term of this patent is extended or adjusted under 35 U.S.C. 154(b) by 1751 days.

(21) Appl. No.: 11/570,740

(22) PCT Filed: Jun. 17, 2005

(86) PCT No.: PCT/CA2005/000942
§ 371 (c)(1),
(2), (4) Date: Aug. 21, 2007

(87) PCT Pub. No.: WO2005/122877
PCT Pub. Date: Dec. 29, 2005

(65) Prior Publication Data
US 2008/0269646 A1    Oct. 30, 2008

Related U.S. Application Data

(63) Continuation-in-part of application No. 10/869,024, filed on Jun. 17, 2004, now abandoned.

(51) Int. Cl.
*A61B 5/11* (2006.01)
*A61B 5/00* (2006.01)

(52) U.S. Cl.
CPC ............... *A61B 5/11* (2013.01); *A61B 5/4205* (2013.01); *A61B 5/6822* (2013.01); *A61B 5/7264* (2013.01); *A61B 2562/0219* (2013.01)

(58) Field of Classification Search
CPC .... A61B 5/4205; A61B 5/04884; A61B 5/42; A61B 5/4233
USPC .......... 600/407, 529, 534, 587, 590, 593, 595
See application file for complete search history.

(56) References Cited

U.S. PATENT DOCUMENTS

| 5,024,240 A | 6/1991 | McConnel |
| 5,143,087 A | 9/1992 | Yarkony |

(Continued)

FOREIGN PATENT DOCUMENTS

| WO | WO 02/26101 A2 | 4/2002 |
| WO | WO 02/082968 A2 | 10/2002 |

(Continued)

OTHER PUBLICATIONS

Chau, Thomas T.K. et al., Testing the stationarity and normality of paediatric aspiration signals, Proceedings of the Second Joint EMBS/BMES Conference, Houston, TX, USA, Oct. 23-26, 2002 (2 pages).

(Continued)

*Primary Examiner* — Adam J Eiseman
(74) *Attorney, Agent, or Firm* — K&L Gates LLP

(57) ABSTRACT

A system and method for detecting swallowing activity is provided. In an embodiment, a method includes receiving an electronic signal from an acceleronic signal from an accelerometer that represents swallowing activity, extracting at least two features from the signal, classifying the signal as a type of swallowing activity based on the extracted features, and generating an output of the classification. Exemplary activities include swallows, aspirations, movement and vocal artifacts. By indicating whether an activity is a swallow or an aspiration, the manner in which a patient afflicted with an increased likelihood for aspirations is fed can be adjusted to increase the likelihood of achieving a swallow instead of an aspiration during feeding. In turn this could reduce hospitalizations for aspiration pneumonia in patients with acute or chronic injury.

19 Claims, 9 Drawing Sheets

(56) References Cited

U.S. PATENT DOCUMENTS

| | | | |
|---|---|---|---|
| 5,263,491 A | 11/1993 | Thornton | |
| 5,274,548 A * | 12/1993 | Bernard et al. | 600/500 |
| 5,445,144 A | 8/1995 | Wodicka et al. | |
| H1557 H | 7/1996 | Joubert et al. | |
| 5,842,997 A * | 12/1998 | Verrier et al. | 600/518 |
| 5,891,185 A | 4/1999 | Freed et al. | |
| 5,970,978 A | 10/1999 | Aviv et al. | |
| 6,267,729 B1 | 7/2001 | Addington et al. | |
| 6,445,942 B1 * | 9/2002 | Berthon-Jones et al. | 600/407 |
| 6,568,397 B1 | 5/2003 | Addington et al. | |
| 6,581,605 B2 | 6/2003 | Addington et al. | |
| 6,620,100 B2 | 9/2003 | Smits et al. | |
| 6,978,787 B1 | 12/2005 | Broniatowski | |
| 7,749,177 B2 * | 7/2010 | Chau et al. | 600/593 |
| 2002/0133194 A1 | 9/2002 | Leelamanit et al. | |
| 2003/0018276 A1 * | 1/2003 | Mansy et al. | 600/529 |
| 2004/0147816 A1 * | 7/2004 | Policker et al. | 600/300 |
| 2006/0064037 A1 * | 3/2006 | Shalon et al. | 600/586 |

FOREIGN PATENT DOCUMENTS

| | | |
|---|---|---|
| WO | WO 2004/011035 A2 | 2/2004 |
| WO | WO 2005/023105 A1 | 3/2005 |

OTHER PUBLICATIONS

Chau, Casas, Berall and Kenny, Poster Presentation, "To characterize normality and stationarity properties of paediatric aspiration signals", Houston, Texas, Oct. 2002 (5 pages).

Silva and Chau, "Coupled microphone-accelerometer sensor pair for dynamic noise reduction to MMG signal recording", Electronics Letters, Oct. 16, 2003, vol. 39, No. 21 (2 pages).

Mayo Clinic website: (1) "Treatment of Aspiration"; and (2) "Frequently Asked Questions about Swallowing", Jacksonville, Florida, Oct. 12, 2003 (2 pages).

The Voice & Swallowing Center website: (1) "Frequently Asked Questions"; and (2) "What's Considered a Swallowing Problem?", College of Physicians & Surgeons, Columbia University, Oct. 12, 2003 (8 pages).

Miyazaki, Arakawa and Kizu, "Introduction of Simple Swallowing Ability Test for Prevention of Aspiration Pneumonia in the Elderly and Investigation of Factors of Swallowing Disorders", 122(1) 97-105 (2002), The Pharmaceutical Society of Japan (9 pages).

The Neuroscience on the Web Series: SPPA 342, Neuropathologies of Swallowing and Speech, CSU, Chico and McCaffrey, "Unit 5. The Nature of the Swallow", Oct. 12, 2003 (4 pages).

Fact Sheet 2, "Tell me about Aspiration and swallowing difficulty in people with a disability", Department of Ageing, Disability & Home Care (4 pages).

Das, Reddy and Narayanan, "Hybrid fuzzy logic committee neural networks for recognition of swallow acceleration signals", Computer Methods and Programs in Biomedicine, 64 (2001) 87-99, Elsevier Science Ireland Ltd. (13 pages).

Reddy, Katakam, Gupta, Unnikrishnan, Narayanan and Canilang, "Measurements of acceleration during videofluorographic evaluation of dysphagic patients", Medical Engineering & Physics; 22 (2000) 405-412, Elsevier Science Ireland Ltd. (8 pages).

Scott, Perry and Bench, "A Study of Interrater Reliability when Using Videofluoroscopy as an Assessment of Swallowing", Dysphagia, 13:223-227 (1998), Springer-Verlag New York Inc. (5 pages).

Leder, Sasaki and Burrell, "Fiberoptic Endoscopic Evaluation of Dysphagia to Identify Silent Aspiration", Dysphagia, 13:19-21 (1998), Springer-Verlag New York Inc. (3 pages).

Martin-Harris, Logemann, McMahon, Schleicher and Sandidge, "Clinical Utility of the Modified Barium Swallow", Dysphagia, 15:136-141 (2000), Springer-Verlag New York Inc. (6 pages).

Laubert, "Zur Diagnostik der postoperativen Dysphagie und Aspiration, Fiberoptisch-endoskopisch kontrollierter Methylen-Blauschluck", HNO, 1999-47:479-484, Springer-Verlag (6 pages).

Leder and Karas, "Fiberoptic Endoscopic Evaluation of Swallowing in Pediatric Population", The Laryngoscope, 110: Jul. 2000, 1132-1136, Lippincott Williams & Wilkins, Inc., Philadelphia, USA (5 pages).

Madden, Fenton, Hughes and Timon, "Comparison between videofluoroscopy and milk-swallow endoscopy in the assessment of swallowing function", Clin. Otolaryngol, 2000, 25, 504-506, Blackwell Science Ltd. (3 pages).

Colodny, "Comparison of Dysphagics and Nondysphagics on Pulse Oximetry during Oral Feeding", Dysphagia, 15:68-73 (2000), Springer-Verlag New York Inc. (6 pages).

Sherman, Nisenboum, Jesberger, Morrow and Jesberger, "Assessment of Dysphagia with the Use of Pulse Oximetry", Dysphagiam 14:152-156 (1999), Springer-Verlag New York Inc. (5 pages).

Lim, Lieu, Phua, Seshadri, Venketasubramanian, Lee and Choo, "Accuracy of Bedside Clinical Methods Compared with Fiberoptic Endoscopic Examination of Swallowing (FEES) in Determining the Risk of Aspiration in Acute Stroke Patients", Dysphagia, 16:1-6 (2001), Springer-Verlag New York Inc. (6 pages).

Sellars, Dunnet and Carter, "A Preliminary Comparison of Videofluoroscopy of Swallow and Pulse Oximetry in the Identification of Aspiration in Dysphagic Patients", Dysphagia, 13:82-86 (1998), Springer-Verlag New York Inc. (5 pages).

Zenner, Losinski and Mills, "Using Cervical Auscultation in the Clinical Dysphagia Examination in Long-Term Care", Dysphagia, 10:27-31 (1995), Springer-Verlag New York Inc. (5 pages).

Cichero and Murdoch, "Detection of Swallowing Sounds: Methodology Revisited", Dysphagia, 17:40-49 (2002), Springer-Verlag New York Inc. (10 pages).

Leder, "Use of Arterial Oxygen Saturation, Heart Rate, and Blood Pressure as Indirect Objective Physiologic Markers to Predict Aspiration", Dysphagia, 15:201-205 (2000), Springer-Verlag New York Inc. (5 pages).

Reddy, Thomas, Canilang and Casterline, "Toward classification of dysphagic patients using biomechanical measurements", Journal of Rehabilitation Research and Development, vol. 31 No. 4, Nov. 1994, pp. 335-344, Department of Veterans Affairs (10 pages).

Stroud A.E., Lawrie, B.W., & Wiles, C.M. (2002). "Inter- and intra-rater reliability of cervical auscultation to detect aspiration in patients with dysphagia." Clinical Rehabilitation, 16, 6, 640-645 (6 pages).

Wright, R.E.R., Wright F.R., & Carson, C.A. (1996). "Videofluoroscopic assessment in children with severe cerebral palsy presenting with dysphagia." Pediatric Radiology, 26, 10, 720-722 (3 pages).

Sonies, B.C. (1994). "Dysphagia: A model for differential diagnosis for adults and children." In L.R. Cherney (Ed.) Clinical Management of Dysphagia in Adults and Children 2nd edition, Gaithersburg, M: Aspen Publishers Inc. (21 pages).

Beck, T.J., & Gayler, B.W. (1991). "Radiation in video-recorded fluoroscopy." In B. Jones & M.W. Donner (Eds.) Normal and Abnormal Swallowing: Imaging in Diagnosis and Therapy. Springer-Verlag (7 pages).

Casas, M.J., Kenny, D.J., Chau, T. and Berall, G., PowerPoint Presentation "Characterization of pediatric aspiration sounds", Jun. 2002 (13 pages).

Bendat, Julius S., Piersol, Allen G, "Random Data," Analysis and Measurement Procedures: Statistical Principles (2000) Chapter 4, pp. 86-117.

Bendat, Julius S., Piersol, Allen G, "Random Data," Analysis and Measurement Procedures: Data Acquisition and Processing (2000) Chapter 10, pp. 349-393.

Wilcox, Rand R, "Introduction to Robust Estimation and Hypothesis Testing," A foundation for Robust Methods (1997) Chapter 2, pp. 11-29.

Bishop, Christopher M. "Neural Networks for Pattern Recognition," Department of Computer Science and Applied Mathematics, Aston University, Birmingham, UK; Calendon Press; Oxford: 1995.

* cited by examiner

SYSTEM AND METHOD FOR DETECTING SWALLOWING ACTIVITY

FIELD OF THE INVENTION

The present invention relates generally to the diagnosis of aspiration and more particularly relates to a system and method for detecting swallowing and related activity.

BACKGROUND OF THE INVENTION

Dysphagia refers to any deglutition (swallowing) disorder, including abnormalities within the oral, pharyngeal and esophageal phases of swallowing. Dysphagia is common in individuals with neurological impairment, due to, for example, cerebral palsy, cerebrovascular accident, brain injury, Parkinson's disease, stroke and multiple sclerosis. Individuals with dysphagia are often at risk of aspiration. Aspiration refers to the entry of foreign material into the airway during inspiration. Aspiration may manifest itself in a number of different ways. The individual may begin to perspire and the face may become flushed. Alternatively, the individual may cough subsequent to swallowing. In silent aspiration, there are no overt clinical or easily recognizable signs of bolus inhalation. The invention is particularly useful for individuals with silent aspiration, but is also applicable for other manifestations of aspiration. Aspiration bears serious health consequences such as chronic lung disease, aspiration pneumonia, dehydration, and malnutrition.

Dysphagia afflicts an estimated fifteen million people in the United States. Certain sources indicate that fifty thousand people die each year from aspiration pneumonia (Dray et al., 1998). The occurrence of diffuse aspiration bronchiolitis in patients with dysphagia is not uncommon, regardless of age (Matsuse et al., 1998). Silent aspiration is especially prominent in children with dysphagia, occurring in an estimated 94% of that population (Arvedson et al., 1994). Half of stroke survivors have swallowing difficulties (Zorowitz & Robinson, 1999), which translates to 500,000 people per year in the United States, (Broniatowski et al., 2001), and aspiration is reported in 75% of these cases while 32% report chest infections (Perry & Love, 2001). The incidence of dysphagia is particularly significant in acute care settings (25-45%), chronic care units (50%) (Finiels et al., 2001) and homes for the aged (68%) (Steele et al., 1997). Dysphagia tremendously diminishes quality of life for people of all ages, compromising not only medical, but social, emotional and psychosocial well-being.

The modified barium swallow using videofluoroscopy is the current gold standard for confirmation of aspiration (Wright et al., 1996). Its clinical utility in dysphagia management continues to be asserted (e.g., Martin-Harris, 2000; Scott et al., 1998). The patient ingests barium-coated material and a video sequence of radiographic images is obtained via X-radiation. The modified barium swallow procedure is invasive and costly both in terms of time and labor (approximately 1,000 health care dollars per procedure in Canada), and renders the patient susceptible to the effects of ionizing radiation (Beck & Gayler, 1991).

Fibreoptic endoscopy, another invasive technique in which a flexible endoscope is inserted transnasally into the hypopharynx, has also been applied in the diagnosis of postoperative aspiration (Brehmer & Laubert, 1999) and bedside identification of silent aspiration (Leder et al., 1998). Fibreoptic endoscopy is generally comparable to the modified barium swallow in terms of sensitivity and specificity for aspiration identification (e.g., Madden et al., 2000; Leder & Karas, 2000), with the advantage of bedside assessment. Pulse oximetry has been proposed as a non-invasive adjunct to bedside assessment of aspiration (e.g., Sherman et al., 1999; Lim et al., 2001). However, several controlled studies comparing pulse oximetric data to videofluorscopic (Sellars et al., 1998) and fiberoptic endoscopic evaluation (Leder, 2000; Colodny, 2000) have raised doubts about the existence of a relationship between arterial oxygen saturation and the occurrence of aspiration.

Cervical auscultation involves listening to the breath sounds near the larynx by way of a laryngeal microphone, stethoscope or accelerometer (Zenner et al., 1995) placed on the neck. It is generally recognized as a limited but valuable tool for aspiration detection and dysphagia assessment in long-term care (Zenner et al., 1995; Cichero & Murdoch, 2002; Stroud et al., 2002). However, when considered against the gold standard of videofluoroscopy, bedside evaluation even with cervical auscultation yields limited accuracy (40-60%) in detecting aspirations (Sherman et al., 1999; Selina et al., 2001; Sellars et al., 1998). Indeed, our recent research shows that aspirations identified by clinicians using cervical auscultation, represent only a quarter of all aspirations (Chau, Casas, Berall & Kenny, submitted).

Swallowing accelerometry (Reddy et al., 2000) is closely related to cervical auscultation, but has entailed digital signal processing and artificial intelligence as discrimination tools, rather than trained clinicians. In clinical studies, accelerometry has demonstrated moderate agreement with videofluoroscopy in identifying aspiration risk (Reddy et al., 1994) where as the signal magnitude has been linked to the extent of laryngeal elevation (Reddy et. al, 2000). Recently, fuzzy committee neural networks have demonstrated extremely high accuracy at classifying normal and "dysphagic" swallows (Das et al., 2001). However, prior art swallowing accelerometry only provides limited information in classifying normal from "dysphagic" swallows and does not provide broader information about the clinical status of the patient.

Administration of videofluoroscopy or nasal endoscopy requires expensive equipment and trained professionals such as a radiologist, otolaryngologist or speech-language pathologist (Sonies, 1994). Invasive procedures are not well-tolerated by children and cannot be practically administered for extended periods of feeding. There is a need for an economical, non-invasive and portable method of aspiration detection, for use at the bedside and outside of the institutional setting.

SUMMARY OF THE INVENTION

It is an object of the present invention to provide a novel system and method for detecting swallowing activity that obviates or mitigates at least one of the above-identified disadvantages of the prior art.

An aspect of the invention provides a method for detecting swallowing activity comprising the steps of:

receiving an electronic signal representing swallowing activity;

extracting at least two features from the signal;

classifying the signal as a type of swallowing activity based on the features; and, generating an output representing the classification.

The electronic signal can be generated by an accelerometer. The features can include at least one of stationarity, normality and dispersion ratio. The classifying step can be performed using a radial basis neural network.

The swallowing activity can include at least one of a swallow and an aspiration.

The extracting step can include stationarity as one of the features, the extracting step of stationarity including the following sub-steps:
   dividing the signal into a plurality of non-overlapping bins;
   determining a total number of total number of reverse arrangements, ($A_{Total}$,) in a mean square sequence is determined;
   extracting the stationarity feature (z), determined according to the following equation:

$$z = \frac{A_{Total} - \mu_A}{\sigma_A}$$

where:
   $\mu_A$ is the mean number of reverse arrangements expected for a stationary signal of the same length.
   $\sigma_A$ is the standard deviation for an equal length stationary signal Each of the bins can be between about one ms and about nine ms in length. Each of the bins can be between about three ms and about seven ms in length. Each of the bins can be about five milliseconds ("ms") in length.

The extracting step can include normality as one of the features, the extracting step of normality including the following sub-steps:
   standardizing the signal to have zero mean and unit variance ("s").
   dividing the standardized signal into a plurality of bins ("I") each of about 0.4 Volts, where $$\left\lceil \frac{max(s) - min(s)}{0.4} \right\rceil,$$

and wherein a highest bin extends to infinity and a lowest bin extends to negative infinity.
   determining observed frequencies ("n") for each the bin by counting the number of samples in the standardized signal ("s") that fell within each the bin.
   determining expected frequencies $\hat{m}$ for each the bin is determined under the assumption of normality, using a Chi-square ($X^2$) statistic using the following:

$$\hat{X}^2 = \sum_{i=1}^{I} \frac{(n_i - \hat{m}_i)^2}{\hat{m}_i}$$

determining the normality feature using the following:

$$\log_{10}(\hat{X}^2)$$

The extracting step can include a dispersion ratio as one of the features, the extracting step of dispersion ratio including the following sub-steps:
   determining a mean absolute deviation of the signal according to the following:

$$S_1 = \frac{1}{n} \sum_{i=1}^{n} |x_i - med(x)|$$

determining an interquartile range, $S_2$, of the signal
   extracting the dispersion ratio according to the following:

$$\frac{S_1}{S_2}$$

Another aspect of the invention provides an apparatus for detecting swallowing activity comprising an input device for receiving an electronic signal from a sensor. The electronic signal can represent swallowing activity. The apparatus also comprises a microcomputer connected to the input device that is operable to extract at least two features from the signal. The microprocessor is further operable to classify the signal as a type of swallowing activity based on the features. The apparatus also includes an output device connected to the microcomputer for generating an output representing the classification.

BRIEF DESCRIPTION OF THE DRAWINGS

The invention will now be described by way of example only, and with reference to the accompanying drawings, in which.

DETAILED DESCRIPTION OF THE INVENTION

As used herein the terms "swallow" and "penetration" are distinguished from the term "aspiration". As used herein, a "swallow" is the safe passage of foodstuffs from the oral cavity, through the hypopharynx and into the esophagus. Further, a swallow is accompanied by a period of apnea with no entry of foodstuffs into the protected airway. "Penetration" is the entry of foreign material into the airway but not accompanied by inspiration. However, "aspiration" is the entry of foreign material into the airway during inspiration. As used in relation to the embodiments discussed below, the term "swallowing activity" means a swallow or an aspiration or the absence of either, but in other embodiments "swallowing activity" can refer to other types of activities including penetration.

Figure 1:
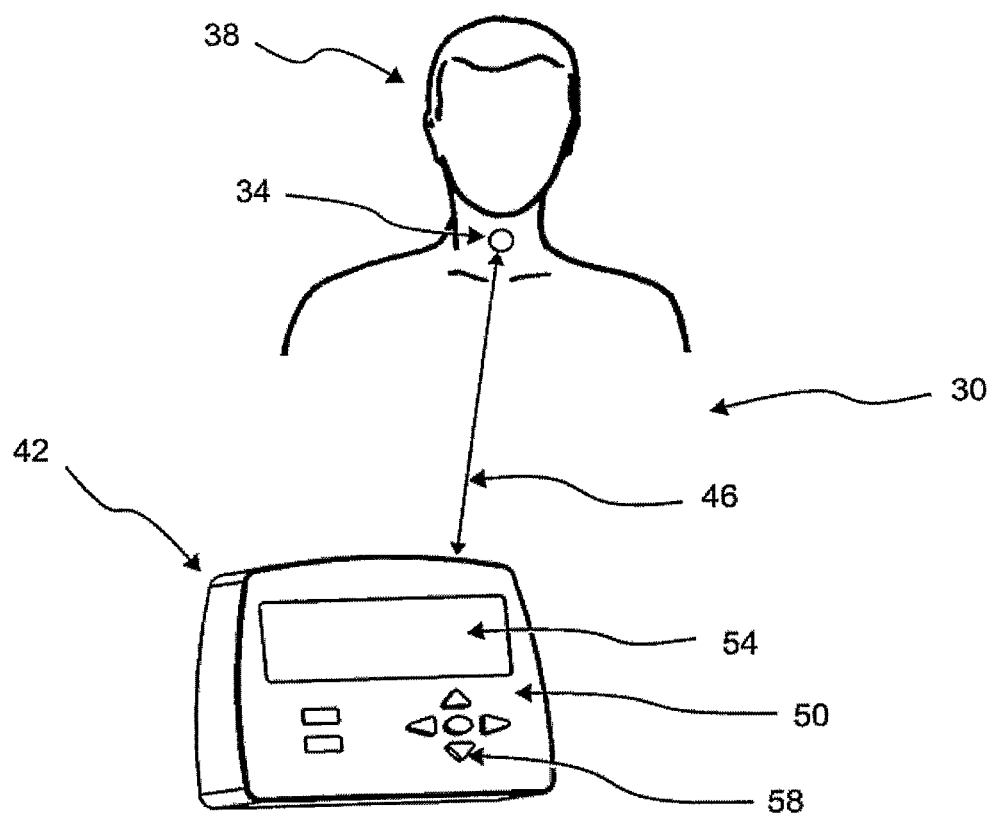
FIG. 1 is a schematic representation of a system for detecting swallowing activity in accordance with an embodiment of the invention.

Referring now to FIG. 1, a system for detecting swallowing activity is indicated generally at 30. System 30 includes an accelerometer 34 that is positioned on the throat of a patient 38. In a present embodiment, accelerometer 34 is placed infer-anterior to the thyroid notch, so that the axis of the accelerometer 34 is aligned to measure anterior-posterior vibrations. System 30 also includes a computing apparatus 42 that is connected to accelerometer 34 via a link 46. Link 46 can be wired or wireless as desired and corresponding to appropriate interfaces on accelerometer 34 and apparatus 42. Link 46 can thus be based on, for example, universal serial bus ("USB"), firewire, RS-232, infra-red, Bluetooth, 802.11 and its variants, Code Division Multiple Access ("CDMA"), orthogonal frequency multiplexing ("OFDM") etc. System 30 is operable to receive acceleration signals from accelerometer 34 that reflect swallowing activity in patient 38.

In a present embodiment, accelerometer 38 is the EMT 25-C single axis accelerometer from Siemens Canada, Mississauga, Ontario Canada ("EMT 25-C"). Other accelerometers that can be used will occur to those of skill in the art.

In a present embodiment, computing apparatus 42 is based on the computing environment and functionality of a specially configured electronic unit that includes a chassis 50 that frames a display 54 for presenting user output and a plurality of keys 58 for receiving user input. Computing apparatus 42 thus includes an interface to allow apparatus 42 to connect to accelerometer 34 via link 46. Computing apparatus 42 thus includes any suitable arrangement of microprocessor, random access memory, non-volatile storage, operating system, etc. As will be explained in greater detail below, computing apparatus 42 is operable to receive signals from accelerometer 34 and to detect swallowing activity from such signals, and report on those activities by presenting output on display 54.

Figure 2:
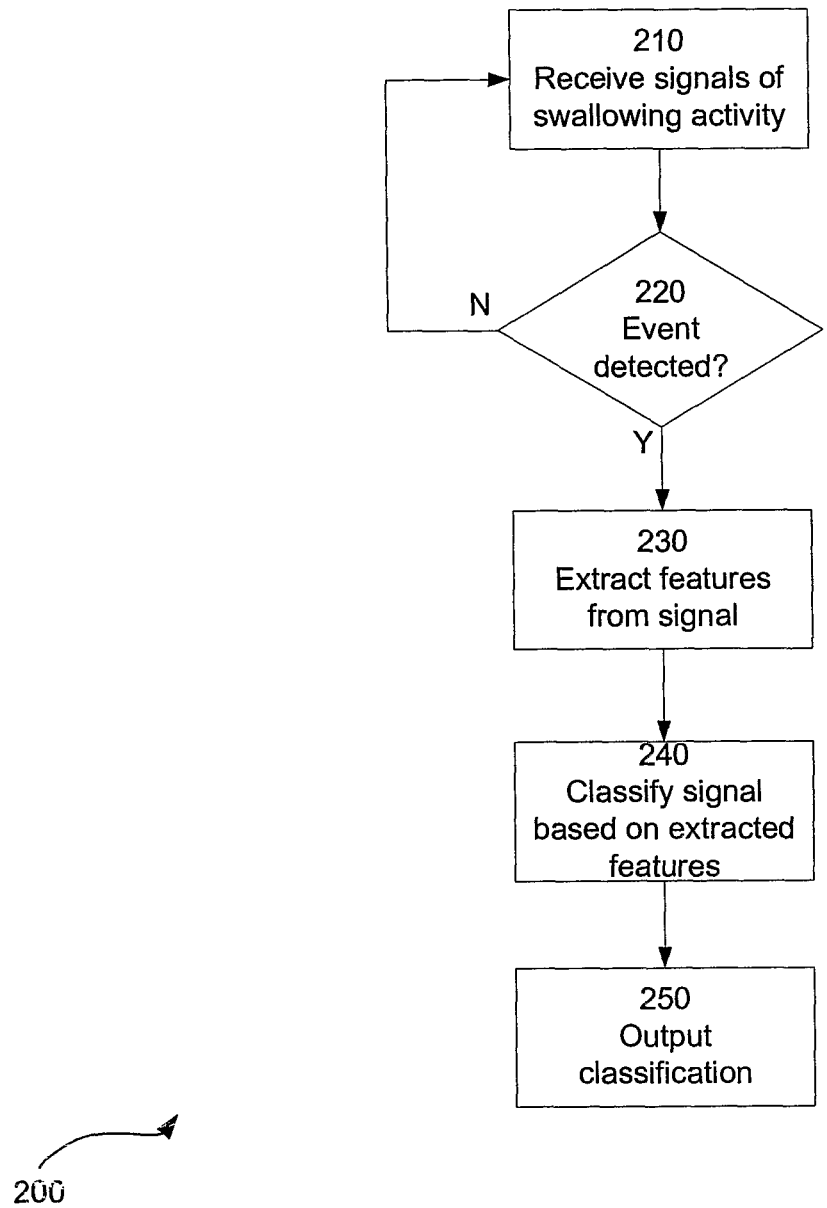
FIG. 2 is a flow chart depicting a method for detecting swallowing activity in accordance with another embodiment of the invention.

In order to help explain certain of these implementations and various other aspects of system 30, reference will now be made to FIG. 2 which shows a method for detecting swallowing activity and which is indicated generally at 200. However, it is to be understood that system 30 and/or method 200 can be varied, and need not work exactly as discussed herein in conjunction with each other, and that such variations are within the scope of the present invention.

Figure 3:
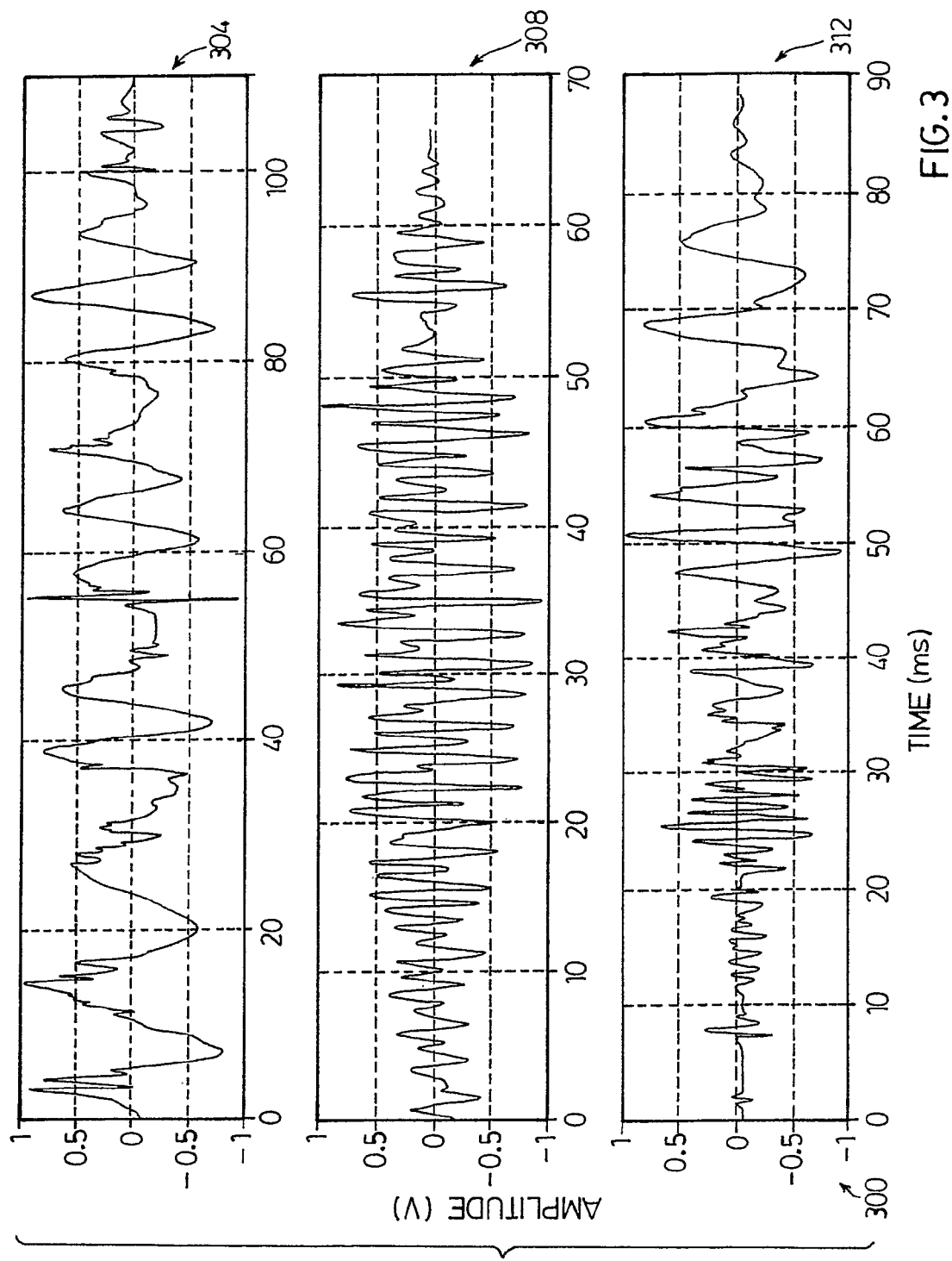
FIG. 3 is a set of graphs showing exemplary signals that can be detected using the system in FIG. 1.

Beginning first at step 210, signals representing swallowing activity are received. When method 200 is implemented using system 30, step 210 refers to the generation of electrical signals by accelerometer 34 and the receipt of those signals at computing apparatus 42. The use of accelerometer 34 means that acceleration signals representing the swallowing activity of patient 38 are received, and due to the unique characteristics of the EMT 25-C accelerometer used in the present embodiment, unique features can be found in the appearance of those signals. FIG. 3 shows examples of signals that can be received using EMT 25-C, indicated generally at 300, and specifically at 304, 308 and 312. Speaking in very general terms, signal 304 is an example of typical pediatric aspiration signals that portray weak or wide-sense stationarity; signal 308 is an aspiration signal that portrays nonstationarity due to evolving variance; and signal 312 is an aspiration signal that portrays nonstationarity due to time-varying frequency and variance structure.

However, it is to be understood that signals 300 are simply raw data, and can represent aspirations or swallows or motion artifact. It has been determined by the inventors that the distribution of median acceleration magnitude is right-skewed for both aspiration and swallows. Due to the skewness of the distribution, gamma distribution is used to estimate the spread and location parameters within signals 300. In particular, the spread a and location b parameters of the gamma distributions for aspirations and swallows that can be associated with signals such as signals 300 are summarized in Table I.

TABLE I

Location and spread of signal accelerations

| Parameter | Aspirations | | Swallows | |
|---|---|---|---|---|
| | Maximum likelihood estimate | 95% confidence interval | Maximum likelihood estimate | 95% confidence interval |
| Spread (a) | 1.3647 g | [0.9343, 1.7952] | 3.642 g | [2.2713, 5.0128] |
| Location (b) | 1.176 g | [0.732, 1.62] | 0.063 g | [0.041, 0.086] |

The stationarity and normality characteristics of signals 300 are summarized in Table II. Stationarity is measured by the nonparametric reverse arrangements tests while normality is measured by a chi-squared distribution-based test of histogram bin counts. Further details about stationarity and normality can be found in "Random Data Analysis and Measurement Procedures" $3^{rd}$ Edition, Julius S. Bendat and Allan G. Pierson, John Wiley & Sons Inc., (c) 2000, New York ("Bendat"), the contents of which are incorporated herein by reference. Chapter 10 of Bendat discusses for tests for stationarity, while Chapter 4 of Bendat discusses with regard to normality.

Table II thus shows a very general, exemplary, summary of how aspirations and swallows can correspond to the stationarity and normality characteristics of received signals such as signals 300.

TABLE II

Stationarity and normality characteristics of signal accelerations

| | Aspirations | Swallows |
|---|---|---|
| Stationarity | 41% not stationary | 46% not stationary |
| Normality | 90% violating normality | 100% violating normality |

Due to the skewness of the distributions of the bandwidths, a gamma distribution is used to determine the location estimate. The frequency bandwidths can be calculated using a discrete wavelet decomposition at ten levels and determining the level at which the cumulative energy (starting from the final level of decomposition) exceeded 85% of the total energy. This determines the 85% bandwidth for the signal in question.

The location estimate (i.e. an estimate of the "mean" value) of the about 85% frequency bandwidth can be between about 700 Hz to about 1100 Hz for aspiration signals, and more preferably can be between about 900 Hz and about 950 Hz, and even more preferably between about 910 Hz and about 940 Hz, and still further preferably about 928 Hz for aspiration signals.

The location estimate of the about 85% frequency bandwidth can be between about 400 Hz to about 700 Hz for swallow signals, and more preferably can be between about 500 Hz and about 650 Hz, and even more preferably between about 590 Hz and about 630 Hz, and still further preferably about 613 Hz for swallows.

Having received signals at step 210, method 200 advances to step 220. At step 220, a determination is made as to whether an event is present inside the signals received at step 210. The criteria for making such a determination is not particularly limited. In a present embodiment, when computing apparatus 42 receives a signal magnitude from accelerometer 34 that exceeds an "on" threshold (in a present embodiment of about 0.025 Volts ("V")) for a pre-determined "onset" period (in a present embodiment about thirty milliseconds ("ms")), event initiation is identified and signal recording begins. The next about 12,000 samples are recorded, corresponding to about 1.2 seconds ("s") of data. Back-trimming is then performed to determine when the signal activity substantially ceased. Such back-trimming involves counting the number of data samples below about 0.05 V, starting from the end of the recording. Once this count exceeds about thirty data points, the end of the useful signal is deemed to have been identified and the end of the signal is trimmed therefrom. In a present embodiment, 12000 samples are recorded, but about 15,000 samples (i.e. about 1.5 s of above threshold signal activity) can also be recorded for analysis as a single signal. In other embodiments other numbers of samples can be recorded, as desired. If the foregoing criteria are not met, then it is determined at step 220 that an event has not occurred and method 200 returns to step 210. However, if the criteria is met then method 200 advances from step 220 to step 230, and the signals that are recorded at step 220 is retained for use at step 230.

Next, at step 230, features are extracted from the recorded signals. In a presently preferred embodiment, stationarity, normality and dispersion ratio are three features that are extracted.

In order to extract the stationarity feature, the procedure in Chapter 10 of Bendat is employed. First, the received signal, is divided into non-overlapping bins each of about five milliseconds ("ms") (i.e. for a total of fifty samples) in length. (The received signal can, however, be divided into non-overlapping bins of between about one ms and about nine ms, or more preferably between about three ms and about seven ms.) Where the signal length, defined herein as "L" is not an integral multiple of fifty, the signal was trimmed at the beginning and end of the signal by approximately (L mod 50)/2. Next, the mean square value within each window was computed. Next, the total number of reverse arrangements, referred to herein as $A_{Total}$, in the mean square sequence is determined. Finally, z-deviate serves as the stationarity feature which is determined according to Equation 1.

$$z = \frac{A_{Total} - \mu_A}{\sigma_A} \qquad \text{Equation 1}$$

where:
$\mu_A$ is the mean number of reverse arrangements expected for a stationary signal of the same length.
$\sigma_A$ is the standard deviation for an equal length stationary signal.

In order to extract the normality feature, an adaptation of the procedure in Chapter 4 of Bendat is employed. First, the signal is standardized to have zero mean and unit variance. The standardized signal is referred to herein as "s". Next, the amplitude of the standardized signal, s, is divided into I bins each of about 0.4 Volts, where $$I = \left\lceil \frac{\max(s) - \min(s)}{0.4} \right\rceil.$$

The highest bin extended to infinity and the lowest bin extended to negative infinity.

Next, the observed frequencies n for each bin are determined by counting the number of samples in the standardized signal that fell within each bin. The expected frequencies $\hat{m}$ for each bin is determined under the assumption of normality. The Chi-square statistic was computed as shown in Equation 2.

$$\hat{X}^2 = \sum_{i=1}^{I} \frac{(n_i - \hat{m}_i)^2}{\hat{m}_i} \qquad \text{Equation 2}$$

Finally, the normality feature is computed as shown in Equation 3.

$$\log_{10}(\hat{X}^2) \qquad \text{Equation 3}$$

In order to determine the dispersion ratio feature, the mean absolute deviation of each signal is determined according to Equation 4.

$$S_1 = \frac{1}{n}\sum_{i=1}^{n}|x_i - med(x)| \qquad \text{Equation 4}$$

Next, the interquartile range, $S_2$, of each signal is determined. The interquartile range is defined in Chapter 2 of "Introduction to robust estimation and hypothesis testing", Rand R. Wilcox, 1997, Academic Press, Calif. Finally, the dispersion ratio feature is determined according to Equation 5.

$$\frac{S_1}{S_2} \qquad \text{Equation 5}$$

Having extracted these features from the signal, method 200 advances to step 240, at which point the signal is classified based on the features extracted at step 230. In a presently preferred embodiment, the classification is performed using a radial basis function neural network implemented on the microcontroller of apparatus 42 to classify swallowing events in real-time, as either swallows or aspirations. Further details about such a radial basis function neural network can be found in Chapter 5 of "Neural Networks for Pattern Recognition", Christopher Bishop, 1995, Clarendon Press, Oxford ("Bishop"), the contents of which are incorporated herein by reference. The network is operable to take the three extracted features as inputs, and output a single number as its classification of the detected type of swallowing activity. In particular, an output level of about 0.1 is assigned to represent swallows and an output level of about 0.9 to represent aspirations. The network architecture consists of three inputs corresponding to each extracted feature, eighty-nine radial basis function units determined from an interactive training procedure as outlined in "Bishop" and one output unit, representing swallowing or aspiration. While eighty-nine radial basis units is presently preferred, in other embodiments from about seventy-five to about one-hundred radial basis units can be used, and in other embodiments from about eighty to about ninety-five radial basis units can be used, all corresponding to one output. The first layer is nonlinear and the second layer is linear. Put in other words, the first layer of the network consists of the nonlinear radial basis functions while the second layer of the network is a weighted linear summation of the radial basis function outputs.

Figure 4:
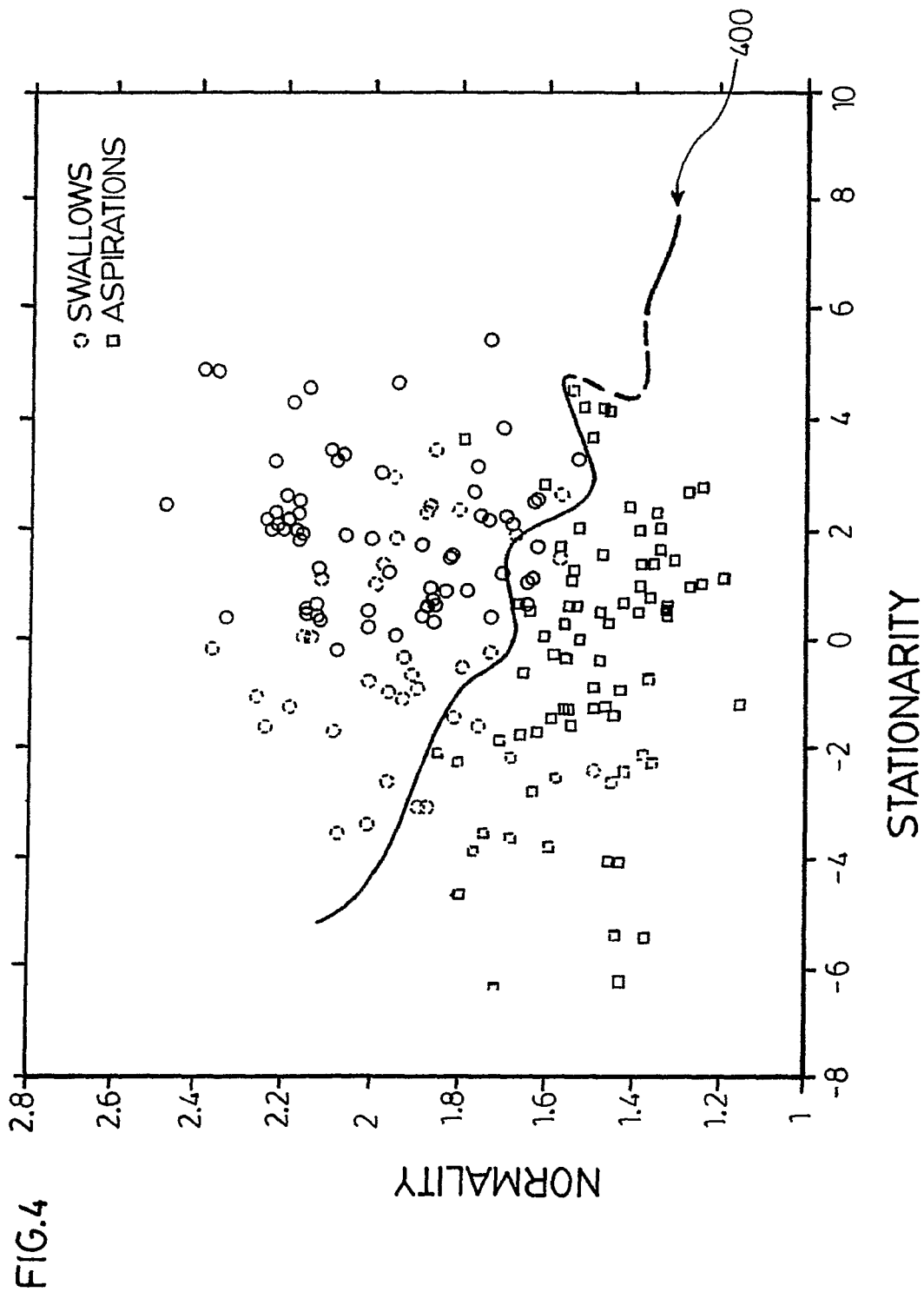
FIG. 4 is a graph showing exemplary output that can be generated by the method in FIG. 2.

Referring now to FIG. 4, a scatter plot is shown for the results of performing steps 210-240 for a number of different signals. The scatter plot in FIG. 4 is only two dimensional, showing only a plot of the stationarity features vs. the normality features. It can be seen that the squares on the scatter plot indicate where aspirations actually occurred, whereas the circles indicate swallows actually occurred. The scatter plot was generated while performing method 200 in conjunction with videofluroscopy so that the actual swallowing activity could be verified, not withstanding the classification performed at step 230, so that the classifications made at step 230 could be verified for accuracy. The line indicated at 400 in FIG. 4 represents a rough dividing line between classifications associated with swallows and aspirations. While some measurements in the scatter plot show a classification that does not reflect the actual type of swallowing activity, the majority of swallowing events are in fact correctly classified. Further improvement to the results shown in FIG. 4 are obtained when the third feature, dispersion ratio, is used to assist in the determination.

Method 200 then advances to step 250, at which point an output is generated corresponding to the classification performed at step 240. Thus, where a particular event was classified as a swallow, then display 54 of apparatus 42 would be instructed to present the message "SWALLOW", whereas if the event was classified as an aspiration then display 54 of apparatus 42 would be instructed to present the message "ASPIRATION". Such messages presented by apparatus 42 could also include colours (e.g. green associated with swallows, red associated with aspirations) and/or auditory signals (e.g. no sound for swallow, beeping for aspirations).

Using method 200, an individual feeding patient 38 can adjust how the feeding is being performed in order to reduce aspirations and increase swallows. Such adjustments to feedings can be based on changing consistency or type of food, the size and/or frequency of mouthfuls being offered to patient 38, and the like.

It should now be understood that as method 200 is implemented using apparatus 42, the microcontroller of apparatus 42 will be provided with software programming instructions corresponding to method 200.

Figure 5:
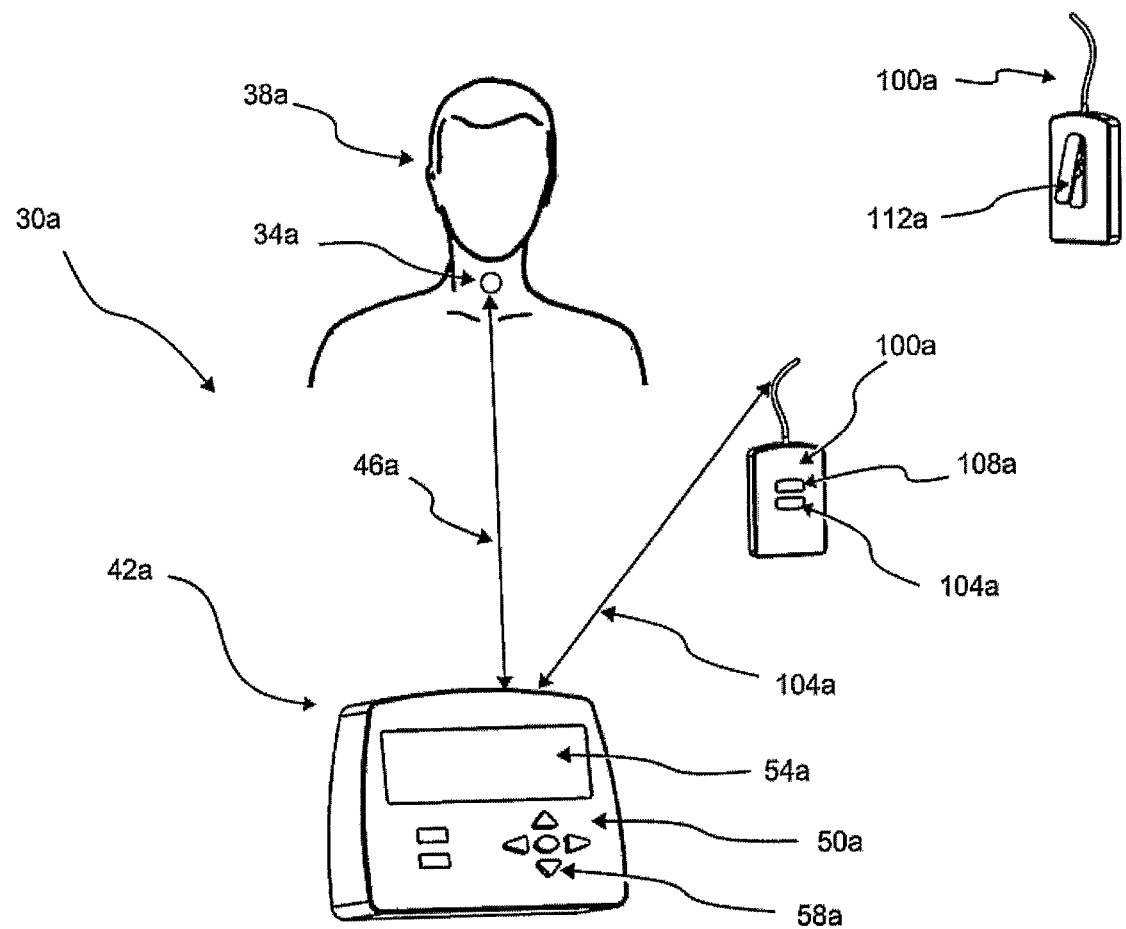
FIG. 5 is a schematic representation of a system for detecting swallowing activity in accordance with an alternative embodiment of the invention.

Referring now to FIG. 5, a system for detecting swallowing activity is indicated generally at 30a. System 30a includes a number of components that are substantially the same as the components in system 30. Accordingly, such like components bear the same reference character except followed by the suffix "a". Of note, system 30a includes a remote unit 100a that is connected via a link 104a to apparatus 42a. Like link 46a, link 104a can either be wired or wireless and based on any desired protocol respective thereto. Also, while link 104a is shown running either directly between unit 100a and apparatus 42a, it should be recognized that if wired, then link 104a can connect apparatus 42a to unit 100a via cabling passing through accelerometer 34a.

Remote unit 100a includes two indicator lights 104a and 108a. On system 30a, step 250 of method 200 is performed using unit 100a. Indicator light 104a is coloured green, and is activated by apparatus 42a to the "on" position to emit a green light when patient 38a successfully swallows. Indicator light 108a is coloured red, and is activated apparatus 42a to the "on" position to emit a green light when patient 38a successfully swallows. Only one indicator light 104a and 108a is "on" at any given time so as not to send confusing messages.

Remote unit 100a also includes an alligator-clip 112a (or other attachment means such as a safety pin or the like) so that unit 100a can be affixed to the collar (or other suitable location) of patient 38a. Unit 100a has many applications. For example, where patient 38a is physically able to feed him/herself (e.g. certain stroke victims), then patient 38a can thus use unit 100a to provide feedback to patient 38a as to whether a swallow or aspiration occurred during a feeding event.

Figure 6:
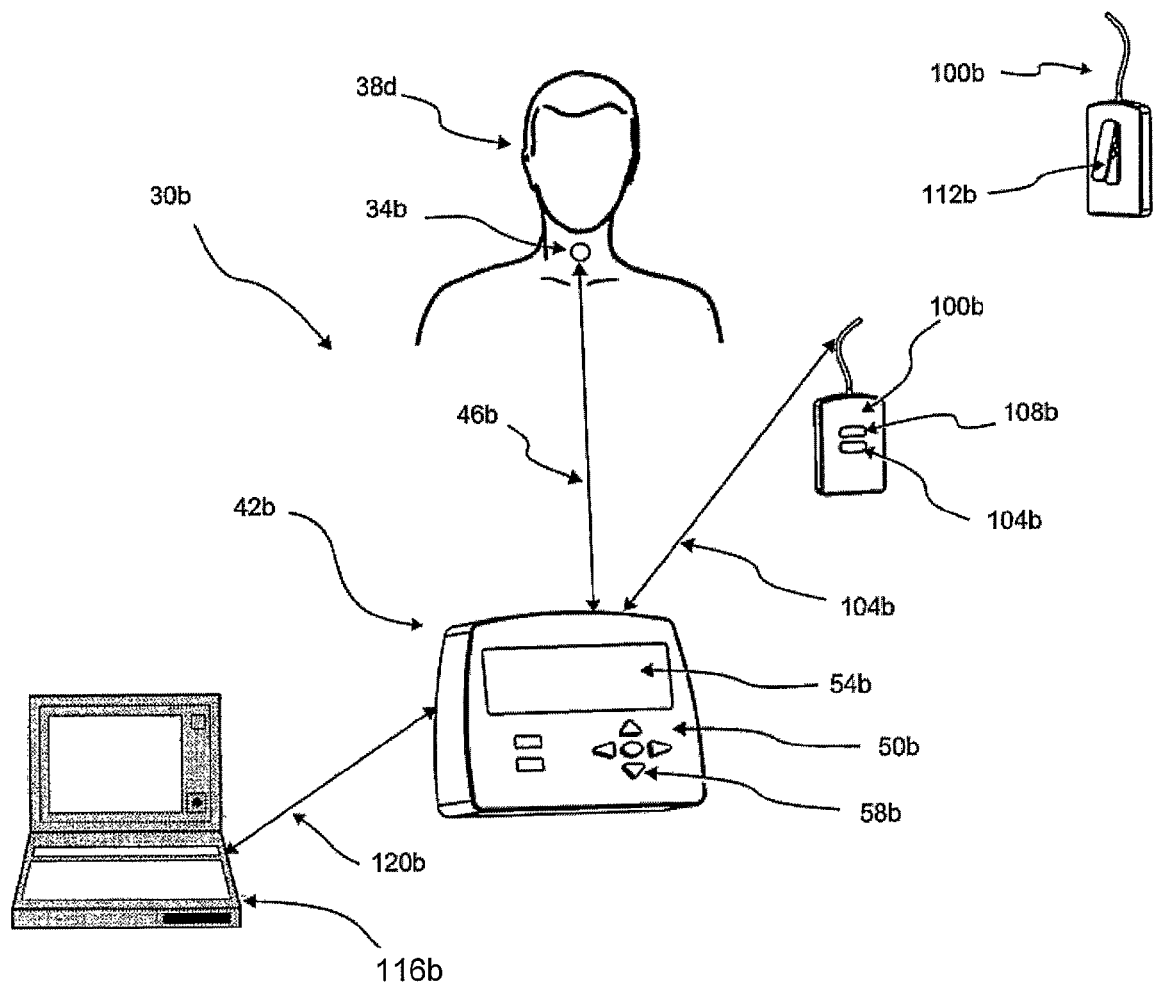
FIG. 6 is a schematic representation of a system for detecting swallowing activity in accordance with another embodiment of the invention.

Referring now to FIG. 6, a system for detecting swallowing activity is indicated generally at 30b. System 30b includes a number of components that are substantially the same as the components in system 30a. Accordingly, such like components bear the same reference character except followed by the suffix "b" instead of the suffix "a". Of note, apparatus 42b includes a persistent storage device, such as a hard disc drive, or flash random access memory, or a smart card, to enable apparatus 42b to record a number of signals such as signal 300, over period of time. The capacity of such a persistent storage device is thus chosen according to the duration of signals that are to be recorded.

System 30b includes a laptop computer 116b that is connected via a link 120b to apparatus 42b. Link 120b can also be wired or wireless and based on any known protocol. Link 120b can be used to download signals that are stored on computer 116b from time to time. In this manner clinicians or other interested parties can utilize laptop computer 116b to analyze such stored signals for any desired purpose. (e.g. patient history; modification or tweaking of processing steps to differentiate different types of swallowing activity etc.).

Link 120b can also be bi-directional, so that updating programming instructions for apparatus 42b can be uploaded to apparatus 42b from laptop computer 116b via link 120b.

Figure 7:
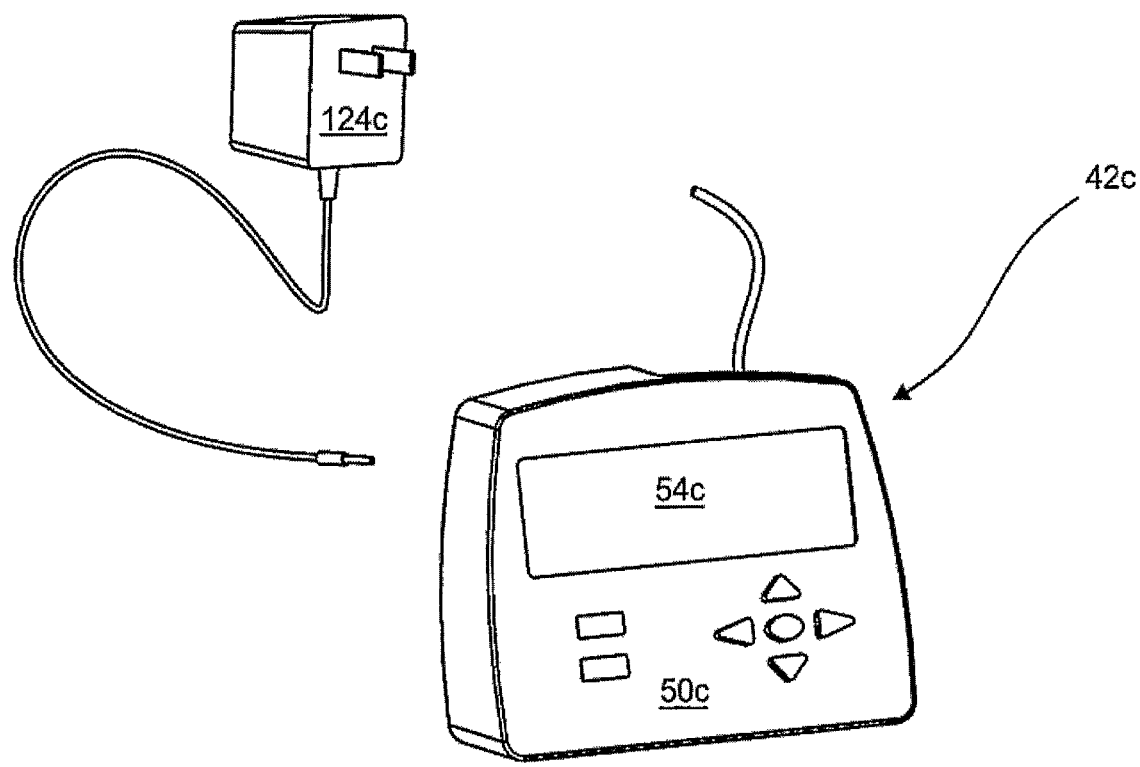
FIG. 7 shows a variation of the apparatus for detecting swallowing activity from the systems in FIGS. 1, 5 and 6 in accordance with another embodiment of the invention.
Figure 8:
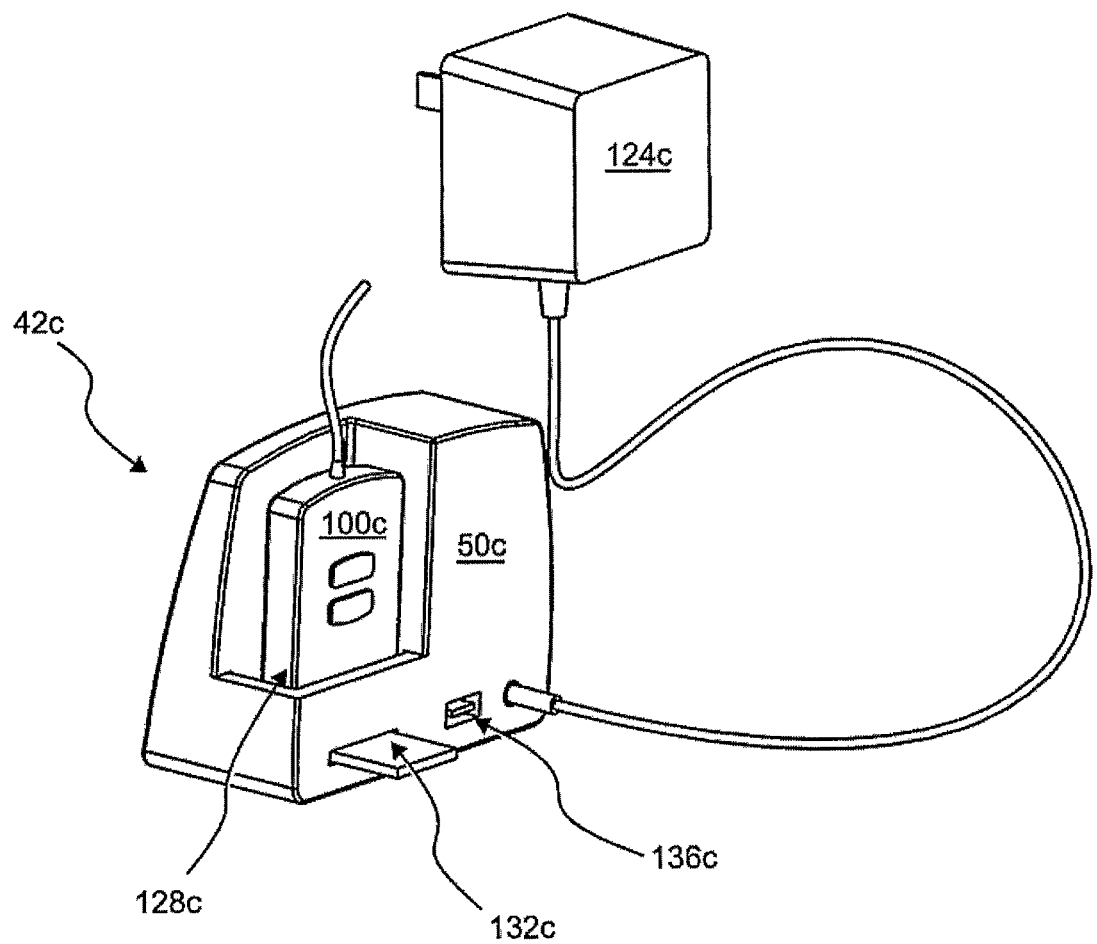
FIG. 8 shows a rear view of the apparatus of FIG. 7.

Referring now to FIGS. 7 and 8, a variation/enhancement on apparatus 42a (and its variant 42b) is indicated at 42c. Apparatus 42c includes a number of components that are substantially the same as the components in apparatus 42a. Accordingly, such like components bear the same reference character except followed by the suffix "c" instead of the suffix "a". Apparatus 42c includes a rechargeable battery (not shown) housed within chassis 50c that powers the internal components of apparatus 42c. The battery is charged via a power supply 124c connectable to apparatus 42c.

As best seen in FIG. 8, apparatus 42c also includes a cradle 128c in which to store unit 100c. Apparatus 42c also includes slot to receive flash memory in a desired format (i.e. Compact Flash™; SD RAM™; Memory Stick™) onto which data can be stored including signals such as signals 300. Also, apparatus 42c includes a pair of universal serial bus ("USB") ports 136 which can be used, for example, for a link such as a link 120b.

Figure 9:
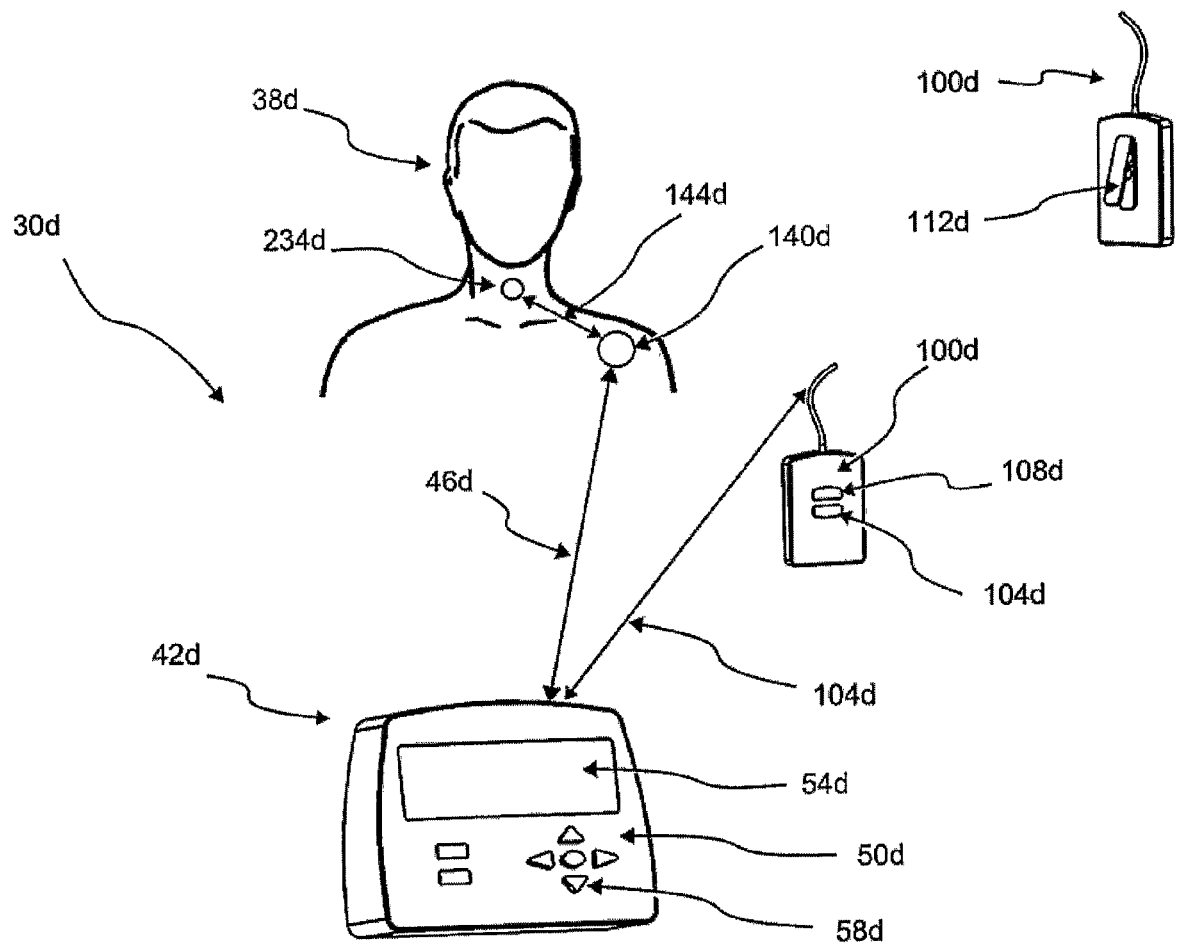
FIG. 9 is a schematic representation of a system for detecting swallowing activity in accordance with another embodiment of the invention.

Referring now to FIG. 9, a system for detecting swallowing activity is indicated generally at 30d. System 30d includes a number of components that are substantially the same as the components in system 30a. Accordingly, such like components bear the same reference character except followed by the suffix "d" instead of the suffix "a". Of note, however, in system 30d sensor 30a is omitted and the functionality of sensor 30a is provided in a distributed manner, wherein a pure accelerometer 234d is affixed to the front of the throat of patient 38d (in the same location as sensor 30a), and a separate processor 140d is connected to accelerometer 234d via a link 144d. Processor 140d receives raw signals from accelerometer 234d and shapes them into signals recognizable to apparatus 42d. Processor 140d is connected to apparatus 42d via link 46d in the same manner as previously provided. in place of a distributed manner, whereby sensor apparatus 42d includes a persistent storage device, such as a hard disc drive, or flash random access memory, or a smart card, to enable apparatus 42b to record a number of signals such as signal 300, over period of time. The capacity of such a persistent storage device is thus chosen according to the duration of signals that are to be recorded.

While only specific combinations of the various features and components of the present invention have been discussed herein, it will be apparent to those of skill in the art that desired subsets of the disclosed features and components and/or alternative combinations of these features and components can be utilized, as desired. For example, of any or all of the features and components of one or more of systems 30, 30*a*, 30*b* and 30*d* and/or apparatus 42*c* can be combined or interchanged as desired.

For example, it is also to be understood that other types of vibration sensors other than accelerometer 34 can be used with appropriate modifications to computing apparatus 42. While presently less preferred, another sensor can include a sensor that measure displacement (e.g microphone), while having computing apparatus 42 record received displacement signals over time. Another type of sensor can include a sensor that measures velocity, having computing apparatus 42 record received velocity signals over time. Such signals can then be converted into acceleration signals and processed according to the above, or other techniques of feature extraction and classification thereof that work with the type of received signal can be employed, as desired.

As another variation, while apparatus 42*c* is shown with a cradle for storing unit 100*c*, apparatus 42 (or its variants) can also include a cradle for storing sensor 34 (or its variants).

As another variation, different versions of method 200 can be simultaneously stored in apparatus 42 (or its variants) and apparatus 42 provided with means for the user to switch between such versions. Such different versions can be directed to extracting different types of features and/or detecting different types of anatomical activity and/or employ differing methods to perform the same result. The user can be given the option of switching to whichever version is desired by the user and/or most suitable to the needs of the particular patient.

As an additional example, while at step 230 of method 200 stationarity, normality and dispersion ratio are three features that are extracted, it is to be understood that in other embodiments other features and/or combinations thereof can be extracted that can be used to detect a swallowing event. For example, while presently less preferred, it can be desired to simply extract any two of stationarity, normality and dispersion ratio in order to make a determination as to whether a particular swallowing event is to be classified as a swallow or aspiration.

As another variation, apparatus 42 can be configured to include "fuzzy logic" wherein apparatus 42 will continue to track signals that are collected and continually update its own criteria for determining whether an aspiration, or swallow, or other swallowing activity was detected.

It should also be understood that other types of anatomical activities of the neck structure, in addition to or in-lieu of swallowing activities such as aspiration and swallowing, can be detected using appropriate modifications of the teachings herein. For example, drooling, trachea muscle tone, turning of the head, vocalizations, coughing, crying, snoring, apnea, breathing. Such activities can be used to detect the existence of or potential for various conditions such as cancer of the larynx, collapsing trachea, sudden infant death ("SIDS") syndrome, and sleep disorders.

As another variation, apparatus 42 can be attached to an output device that will provide bio-stimulus responsive to a detected type of activity—e.g. a device to stimulate a cough when an aspiration is detected.

It should also be understood that other types of features can be extracted in order to ascertain a particular type of anatomical activity, including maximum peak frequency, median frequency, autocorrelation decay rate, skewness, kurtosis and the like. Further, other classification methods can be used including mixture of Gaussians, generalized regression network, probabilistic network, multilayer feed-forward network, linear discriminant function, neuro-fuzzy networks.

Furthermore, while apparatus 42 (and its variants 42*a*, 42*b*, 42*c* and 42*d*) is an electronic device that includes circuitry programmed and/or configured to process signals from an accelerometer (or other sensor) such that it is operable to classify those signals as different types of swallowing activity in other embodiments apparatus 42 can be based on a variety of different computing environments, such as a personal digital assistant or notebook computer having a special software application. Similarly, the device can simply include a set of indicator lights—e.g. a pair of indicator lights, one light for indicating a swallow, the other for indicating an aspiration. Whatever the format of apparatus 42, apparatus 42 can also include an interface for connection to a personal computer or other computing device so that updated programming instructions for detecting aspirations, swallows and/or other types of swallowing activity can be uploaded thereto.

The above-described embodiments of the invention are intended to be examples of the present invention and alterations and modifications may be effected thereto, by those of skill in the art, without departing from the scope of the invention which is defined solely by the claims appended hereto.

The invention claimed is:

1. A method for detecting swallowing activity including aspirations and swallows comprising the steps of:
receiving an electronic acceleration signal generated by a sensor positioned on the throat of a patient, said signal representing swallowing activity;
extracting features from said signal, wherein said features comprise stationarity, normality and dispersion ratio;
wherein the extracting the features comprises determining a mean absolute deviation ("$S_1$") of the electronic acceleration signal according to the following equation:

$$S_1 = \frac{1}{n}\sum_{i=1}^{n} |x_i - med(x)|$$

determining an interquartile range ("$S_2$") of the electronic acceleration signal; and
extracting the dispersion ratio according to the following equation:

$$\frac{S_1}{S_2};$$

applying a radial basis neural network based on the features for classifying said signal as representing an aspiration when an aspiration is detected and as representing a swallow when a swallow is detected; and
generating an output representing one of a swallow and an aspiration.

2. The method of claim 1 wherein the features extracted from said signal consist of the stationarity, the normality and the dispersion ratio.

3. A method for detecting swallowing activity including aspirations and swallows comprising the steps of:
receiving an electronic acceleration signal generated by a sensor positioned on the throat of a patient, said signal representing swallowing activity;

extracting from said signal, wherein said features comprise stationarity, normality and dispersion ratio;
applying a radial basis neural network for classifying said signal as representing an aspiration when an aspiration is detected and as representing a swallow when a swallow is detected; and
generating an output representing one of a swallow and an aspiration;
wherein said extracting the stationarity comprises:
dividing said signal into a plurality of non-overlapping bins;
determining a total number of total number of reverse arrangements, ($A_{Total}$) in a mean square sequence is determined;
extracting said stationarity feature (z), determined according to the following equation:
where:

$$z = \frac{A_{Total} - \mu_A}{\sigma_A}$$

where:
$\mu_A$ is the mean number of reverse arrangements expected for a stationary signal of the same length, and
$\sigma_A$ is the standard deviation for an equal length stationary signal;
wherein said extracting the dispersion ratio comprises determining a mean absolute deviation ("$S_1$") of the electronic acceleration signal according to the following equation:

$$S_1 = \frac{1}{n}\sum_{i=1}^{n}|x_i - med(x)|$$

determining an interquartile range ("$S_2$") of the electronic acceleration signal; and
extracting the dispersion ratio according to the following equation:

$$\frac{S_1}{S_2}.$$

4. A method for detecting swallowing activity including aspirations and swallows comprising the steps of:
receiving an electronic acceleration signal generated by a sensor positioned on the throat of a patient, said signal representing swallowing activity;
extracting features from said signal, wherein said features comprise stationarity, normality and dispersion ratio;
applying a radial basis neural network for classifying said signal as representing an aspiration when an aspiration is detected and as representing a swallow when a swallow is detected; and
generating an output representing one of a swallow and an aspiration;
wherein said extracting the normality comprises:
standardizing the electronic acceleration signal to have zero mean and unit variance ("s");
dividing the standardized electronic acceleration signal into a plurality of bins ("l") of about 0.4 Volts each,
where l=(max(s)−min(s))/0.4, and wherein a highest bin extends to infinity and a lowest bin extends to negative infinity;
determining observed frequencies ("n") for each bin by counting a number of samples in the standardized electronic acceleration signal ("s") that fell within each bin;
determining expected frequencies ("m̂") for each bin is determined under an assumption of normality, using a Chi-square ($X^2$) statistic of:

$$\hat{X}^2 = \sum_{i=1}^{l}\frac{(n_i - \hat{m}_i)^2}{\hat{m}_i}$$

and
determining the normality feature using the following equation:

$\log_{10}(\hat{X}^2)$;

wherein said extracting the dispersion ratio comprises determining a mean absolute deviation ("$S_1$") of the electronic acceleration signal according to the following equation:

$$S_1 = \frac{1}{n}\sum_{i=1}^{n}|x_i - med(x)|$$

determining an interquartile range ("$S_2$") of the electronic acceleration signal; and
extracting the dispersion ratio according to the following equation:

$$\frac{S_1}{S_2}.$$

5. A method for detecting swallowing activity including aspirations and swallows comprising the steps of:
receiving an electronic acceleration signal generated by a sensor positioned on the throat of a patient, said signal representing swallowing activity;
extracting at least two features from said signal, wherein said at least two features include at least one of stationarity, normality and dispersion ratio;
applying a radial basis neural network for classifying said signal as representing an aspiration when an aspiration is detected and as representing a swallow when a swallow is detected; and
generating an output representing one of a swallow and an aspiration;
wherein the extracting at least two features from the electronic acceleration signal includes extracting a dispersion ratio, and the method further comprises:
determining a mean absolute deviation ("$S_1$") of the electronic acceleration signal according to the following equation:

$$S_1 = \frac{1}{n}\sum_{i=1}^{n}|x_i - med(x)|$$

determining an interquartile range ("$S_2$") of the electronic acceleration signal; and extracting the dispersion ratio according to the following equation:

$$\frac{S_1}{S_2}.$$

6. An apparatus for detecting swallowing activity including aspirations and swallows comprising:
- an input device for receiving an electronic signal from one of an accelerometer, a microphone or a velocity sensor, said electronic signal representing swallowing activity;
- a microcomputer connected to said input device and operable to extract features from said signal, said features comprising stationarity, normality and dispersion ratio, wherein said extracting the dispersion ratio comprises determining a mean absolute deviation ("$S_1$") of the electronic signal according to the following equation:

$$S_1 = \frac{1}{n}\sum_{i=1}^{n}|x_i - med(x)|$$

determining an interquartile range ("$S_2$") of the electronic signal; and extracting the dispersion ratio according to the following equation:

$$\frac{S_1}{S_2};$$

said microcomputer further operable to classify said signal as representing an aspiration when an aspiration is detected and as representing a swallow when a swallow is detected using a radial basis neural network based on said features; and
an output device connected to said microcomputer for generating an output representing said classification as a swallow or an aspiration.

7. The apparatus of claim 6 wherein the microcomputer is configured to extract the stationarity, the normality and the dispersion ratio from the signal and configured to use the stationarity, the normality and the dispersion ratio as inputs for the radial basis neural network to obtain a single number output that classifies the signal as representing an aspiration when an aspiration is detected and as representing a swallow when a swallow is detected.

8. An apparatus for detecting swallowing activity including aspirations and swallows comprising:
- an input device for receiving an electronic signal from one of an accelerometer, a microphone or a velocity sensor, said electronic signal representing swallowing activity;
- a microcomputer connected to said input device and operable to extract features from said signal, said features comprising stationarity, normality and dispersion ratio; said microcomputer further operable to classify said signal as representing an aspiration when an aspiration is detected and as representing a swallow when a swallow is detected using a radial basis neural network based on said features; and
- an output device connected to said microcomputer for generating an output representing said classification as a swallow or an aspiration;
- wherein said extracting of the stationarity comprises:
- dividing said signal into a plurality of non-overlapping bins;
- determining a total number of total number of reverse arrangements, ($A_{Total}$) in a mean square sequence is determined;
- extracting said stationarity feature (z), determined according to the following equation:
where:

$$z = \frac{A_{Total} - \mu_A}{\sigma_A}$$

where:
- $\mu_A$ is the mean number of reverse arrangements expected for a stationary signal of the same length, and
- $\sigma_A$ is the standard deviation for an equal length stationary signal;
- wherein said extracting the dispersion ratio comprises determining a mean absolute deviation ("$S_1$") of the electronic signal according to the following equation:

$$S_1 = \frac{1}{n}\sum_{i=1}^{n}|x_i - med(x)|$$

determining an interquartile range ("$S_2$") of the electronic signal; and extracting the dispersion ratio according to the following equation:

$$\frac{S_1}{S_2}.$$

9. An apparatus for detecting swallowing activity including aspirations and swallows comprising:
- an input device for receiving an electronic signal from one of an accelerometer, a microphone or a velocity sensor, said electronic signal representing swallowing activity;
- a microcomputer connected to said input device and operable to extract features from said signal, said features comprising stationarity, normality and dispersion ratio; said microcomputer further operable to classify said signal as representing an aspiration when an aspiration is detected and as representing a swallow when a swallow is detected using a radial basis neural network based on said features; and
- an output device connected to said microcomputer for generating an output representing said classification as a swallow or an aspiration;
- wherein said extracting of the normality comprises:
- standardizing the electronic signal to have zero mean and unit variance ("s");
- dividing the electronic standardized signal into a plurality of bins ("l") each of about 0.4 Volts, where l=(max(s)−min(s))/0.4, and wherein a highest bin extends to infinity and a lowest bin extends to negative infinity;
- determining observed frequencies ("n") for each bin by counting the number of samples in the standardized electronic signal ("s") that fell within each bin;

determining expected frequencies ("$\hat{m}$") for each bin under an assumption of normality, using a Chi-square ($X^2$) statistic of:

$$\hat{X}^2 = \sum_{i=1}^{l} \frac{(n_i - \hat{m}_i)^2}{\hat{m}_i};$$

and determining said normality feature using the following equation:

$$\log_{10}(\hat{X}^2);$$

wherein said extracting the dispersion ratio comprises determining a mean absolute deviation ("$S_1$") of the electronic signal according to the following equation:

$$S_1 = \frac{1}{n} \sum_{i=1}^{n} |x_i - med(x)|$$

determining an interquartile range ("$S_2$") of the electronic signal; and extracting the dispersion ratio according to the following equation:

$$\frac{S_1}{S_2}.$$

10. An apparatus for detecting swallowing activity including aspirations and swallows comprising:
- an input device for receiving an electronic signal from one of an accelerometer, a microphone or a velocity sensor, said electronic signal representing swallowing activity;
- a microcomputer connected to said input device and operable to extract at least two features from said signal, said at least two features comprising one of stationarity, normality and dispersion ratio; said microcomputer further operable to classify said signal as representing an aspiration when an aspiration is detected and as representing a swallow when a swallow is detected using a radial basis neural network based on said features; and
- an output device connected to said microcomputer for generating an output representing said classification as a swallow or an aspiration;
- wherein said extracting includes dispersion ratio as one of said features, said dispersion ratio including:
- determining a mean absolute deviation of the electronic signal according to the following equation:

$$S_1 = \frac{1}{n} \sum_{i=1}^{n} |x_i - med(x)|$$

determining an interquartile range, $S_2$, of the electronic signal; and extracting said dispersion ratio according to the following equation:

$$\frac{S_1}{S_2}.$$

11. A system for detecting one of a plurality of anatomical activities of a neck structure of a living being, said system comprising:
- a sensor for attachment to said neck structure and for generating a signal representing said at least one of a plurality of anatomical activities;
- a computing apparatus connectable to sensor; said computing apparatus including an input device for receiving said signal; a microcomputer connected to said input device and operable to extract features from said signal, said features comprising stationarity, normality and dispersion ratio; said microcomputer being further operable to classify said signal as representing one of said plurality of the anatomical activities based on said features using a radial basis neural network; and
- an output device connected to said microcomputer for generating an output representing said classification;
- wherein said extracting the dispersion ratio comprises determining a mean absolute deviation ("$S_1$") of the signal according to the following equation:

$$S_1 = \frac{1}{n} \sum_{i=1}^{n} |x_i - med(x)|$$

determining an interquartile range ("$S_2$") of the signal; and extracting the dispersion ratio according to the following equation:

$$\frac{S_1}{S_2}.$$

12. The system of claim 11 wherein said type of activity includes at least one of drooling, trachea muscle tone, turning of the head, vocalizations, coughing, crying, snoring, apnea and breathing.

13. The system of claim 11 wherein said type of activity is an indicator of cancer of the larynx.

14. The system of claim 11 wherein said type of activity is an indicator of collapsing trachea.

15. The system of claim 11 wherein said type of activity is an indicator of sudden infant death syndrome.

16. The system of claim 11 wherein said type of activity is an indicator of sleep disorders.

17. The system of claim 11 wherein said output device provides biostimulus response to said classification.

18. The system of claim 11 wherein said output device stimulates a cough in response to an aspiration being detected as said type of activity.

19. The system of claim 11 wherein the microcomputer is configured to extract the stationarity, the normality and the dispersion ratio from the signal and configured to use the stationarity, the normality and the dispersion ratio as inputs for the radial basis neural network to obtain a single number output that classifies the signal as representing an aspiration when an aspiration is detected and as representing a swallow when a swallow is detected.

\* \* \* \* \*